United States Patent [19]
Ahluwalia et al.

[11] Patent Number: 6,093,748
[45] Date of Patent: Jul. 25, 2000

[54] INHIBITION OF HAIR GROWTH

[76] Inventors: Gurpreet S. Ahluwalia, 8632 Stable View Ct., Gaithersburg, Md. 20879; Peter Styczynski, 3709 Roop Rd., New Windsor, Md. 21776; Douglas Shander, 16112 Howard Landing Dr., Gaithersburg, Md. 20878

[21] Appl. No.: 08/963,227

[22] Filed: Nov. 3, 1997

Related U.S. Application Data

[63] Continuation of application No. 08/396,446, Feb. 28, 1995, abandoned.

[51] Int. Cl.[7] .................... A61K 7/06; A61K 7/48
[52] U.S. Cl. .................. 514/880; 424/74; 514/230; 514/844; 514/874
[58] Field of Search .................. 424/73; 514/230, 514/844, 874, 880

[56] References Cited

U.S. PATENT DOCUMENTS

| | | |
|---|---|---|
| 3,426,137 | 2/1969 | Philpitt et al. . |
| 4,039,669 | 8/1977 | Beyler et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,344,941 | 8/1982 | Wiechert et al. . |
| 4,370,315 | 1/1983 | Greff et al. . |
| 4,439,432 | 3/1984 | Peat . |
| 4,720,489 | 1/1988 | Shander . |
| 4,885,289 | 12/1989 | Breuer et al. . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Heverhagen . |
| 5,300,284 | 4/1994 | Wiechers et al. . |
| 5,364,885 | 11/1994 | Ahluwalia et al. . |
| 5,378,455 | 1/1995 | Kealey et al. .................. 424/73 |
| 5,407,944 | 4/1995 | Goldman .................... 514/310 |
| 5,554,608 | 9/1996 | Ahluwalia et al. . |
| 5,753,612 | 5/1998 | Mitrani ........................ 514/2 |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 2753375 A1 | 3/1998 | France . |
| 07112923 | 5/1995 | Japan . |
| 1 458 349 | 12/1976 | United Kingdom . |
| WO 90/12577 | 11/1990 | WIPO . |
| WO 94/04143 | 3/1994 | WIPO . |
| WO 94/27563 | 12/1994 | WIPO . |
| WO 94/27586 | 12/1994 | WIPO . |
| 97/41844 | 11/1997 | WIPO . |

OTHER PUBLICATIONS

Lissak et al. Treatment of Hirsutism with Cimetidine: A Prospective Randomized Controlled Trial. Fertil–Steril. vol. 51, No. 2, pp. 247–250. Feb. 1989.

Golditch et al. Treatment of Hirsutism with Cimetidine. Obstetrics & Gynecology, vol. 75, No. 6, pp. 911–913. Jun. 1990.

Harmon et al., "12–O–Tetradecanoylphorbol–13–Acetate Inhibits Human Hair Follicle Growth and Hair Fiber Production in Whole–Organ Cultures", *SID Abstracts*, 102:533 (Apr., 1994).

Simpson et al., "The effect of topically applied progesterone on sebum excretion rate", *British Journal, of Dermatology*, 100:687–692 (1979).

(List continued on next page.)

*Primary Examiner*—Robert H. Harrison
*Attorney, Agent, or Firm*—Fish & Richardson P.C.

[57] ABSTRACT

A method of inhibiting hair growth in a mammal includes applying, to an area of skin from which reduced hair growth is desired, a dermatologically acceptable composition containing a non-steroidal suppressor of angiogenesis.

88 Claims, 1 Drawing Sheet

OTHER PUBLICATIONS

Messenger, "The Control of Hair Growth: An Overview", *Journal of Investigative Dermatology*, 101:4S–9S (Jul., 1993).

Cohen, "A platelet–activating factor antagonist reduces corneal allograft inflammation and neovascularization", *Current Eye Research*, 13:139–144 (1994).

Sorbo et al., "Mast–cell histamine is angiogenic through receptors for histamine$_1$ and histamine$_2$", *Int. J. Exp. Path.*, 75:43–50 (1994).

Laniado–Schwartzman et al., "Activation Nuclear Factor kB and Oncogene Expression by 12(R)–Hydroxyeicosatrienoic Acid . . . ", *The Journal of Biological Chemistry*, 269:24321–24327 (1994).

Ziche et al., "Role of Prostaglandin E$_1$ and Copper in Angiogenesis[1,2]", *JNCI*, 69:475–480 (1982).

Sato, "The Hair Cycle and its Control Mechanism", *Biology and Disease of the Hair*, 3–13 (1975).

Takano et al., "A Diaminoanthraquinone Inhibitor of Angiogenesis", *The Journal of Pharmacology and Experimental Therapeutics*, 271:1027–1033 (1994).

Borgström et al., "The quinoline–3–carboxamide Linomide inhibits angiogenesis in vivo", *Cancer Chemotherapy and Pharmacology*, 34:280–286 (1994).

Folkman et al., "Minireview: Angiogenesis", *The Journal of Biological Chemistry*, 267:10931–10934 (1992).

Gullino, "Considerations on the Mechanism of the Angiogenic Response", *Anticancer Research*, 6:153–158 (1986).

Raju et al., "Ceruloplasmin, Copper Ions, and Angiogenesis[1,2]", *JNCI*, 69:1183–1188.

Li et al., "Diminished Heparin Binding of a Basic Fibroblast Growth Factor Mutant Is Associated with . . . ", *Biochemistry*, 33:10999–11007 (1994).

Le Noble et al., "Angiotensin II stimulates angiogenesis in the chorio–allantoic membrane of the chick embryo", *European Journal of Pharmacology*, 195:305–306 (1991).

Fan et al., "Stimulation of angiogenesis by substance P and interleukin–1 in the rat and its inhibition . . . ", *Br. J. Pharmacol.*, 110:43–49 (1993).

Wester et al., "Dihydropyridines: A New Class of Angiotensin II Antagonists", *Bioorganic & Medicinal Chemistry Letters*, 4:133–138 (1994).

Poss et al., "1,4–Substituted Indoles: A Potent and Selective Class of Angiotensin II Receptor Antagonists", *Bioorganic & Medicinal Chemistry Letters*, 4:145–150 (1994).

Siegl et al., "In Vivo Pharmacology of L–158,809, a New Highly Potent and Selective Nonpeptide . . . ", *The Journal of Pharmacology and Experimental Therapeutics*, 262:139–144 (1992).

Chang et al., "Triazolinones as Nonpeptide Angiotensin II Antagonists. 2. Discovery of a Potent and . . . ", *Bioorganic & Medicinal Chemistry Letters*, 4:115–120 (1994).

CA113(15):126168f of Hear. Res. 46(1–2), 101–12 (1990).

Shander et al., "Method of Reducing Hair Growth Employing Sulfhydryl Active Compounds", U.S. Patent No. 5,411,991, issued May 2, 1995.

Alluwalia et al., "Inhibition of Hair Growth", U.S.S.N. 08/213,954, allowed.

Ahluwalia, "Method of Reducing the Rate of Hair Growth", U.S.S.N. 08/212,584, allowed.

Burdick et al., "The Topical Effect of the Antiandrogen Chlormadin—One Acetate and Some of its . . . ", *Br. J. Derm.*, 82:19–25 Supplemetn 6, 19 (1970).

Goos et al., "An Improved Method for Evaluating Antiandrogens", *Arch. Dermatol. Res.*, 273:333–341 (1982).

Ushmorov et al., "Effects of Complete and Imcomplete Tumor Promoters on Hair Growth, Angiogenesis, and Tenascin Expression in the Skin of NMRI Mice", *Carcinogenesis*, 15:2739–2745, 1994.

Nguyen et al., "Pentosan Inhibits Angiogenesis In Vitro and Suppresses Prostate Tumor Growth In Vivo", Chemical Abstracts, 120:35, 1994, see abstract; Anticancer Research, 13:2143–2147, 1993.

Arias et al., "Effects of Cyproterone and Tamoxifen Upon the Hair Waves in Mice", Chemical Abstracts, 99:101, 1083, see abstract; ACTA Physiol. Latinoam., 32:261–266, 1982.

Majewski et al., "Relationship Between the Hair Growth Cycle and the Intensity of Lymphocyte–Induced Angiogenesis in Mouse Skin", 277:77–78, 1985.

Paus, "Hair Grwoth Inhibition by Heparin in Mice: A Model System for Studying the Modulation of Epithelial Cell Growth by Glucosaminoglycans?", British Journal of Dermatology, 124:415–422, 1991.

Westgate et al., "Distribution of Proteoglycans During the Hair Growth Cycle in Human Skin", The J. of Investigative Dermatology, 96:191–195, 1991.

Notification of Transmittal of The International Search Report or the Declaration (8 pages).

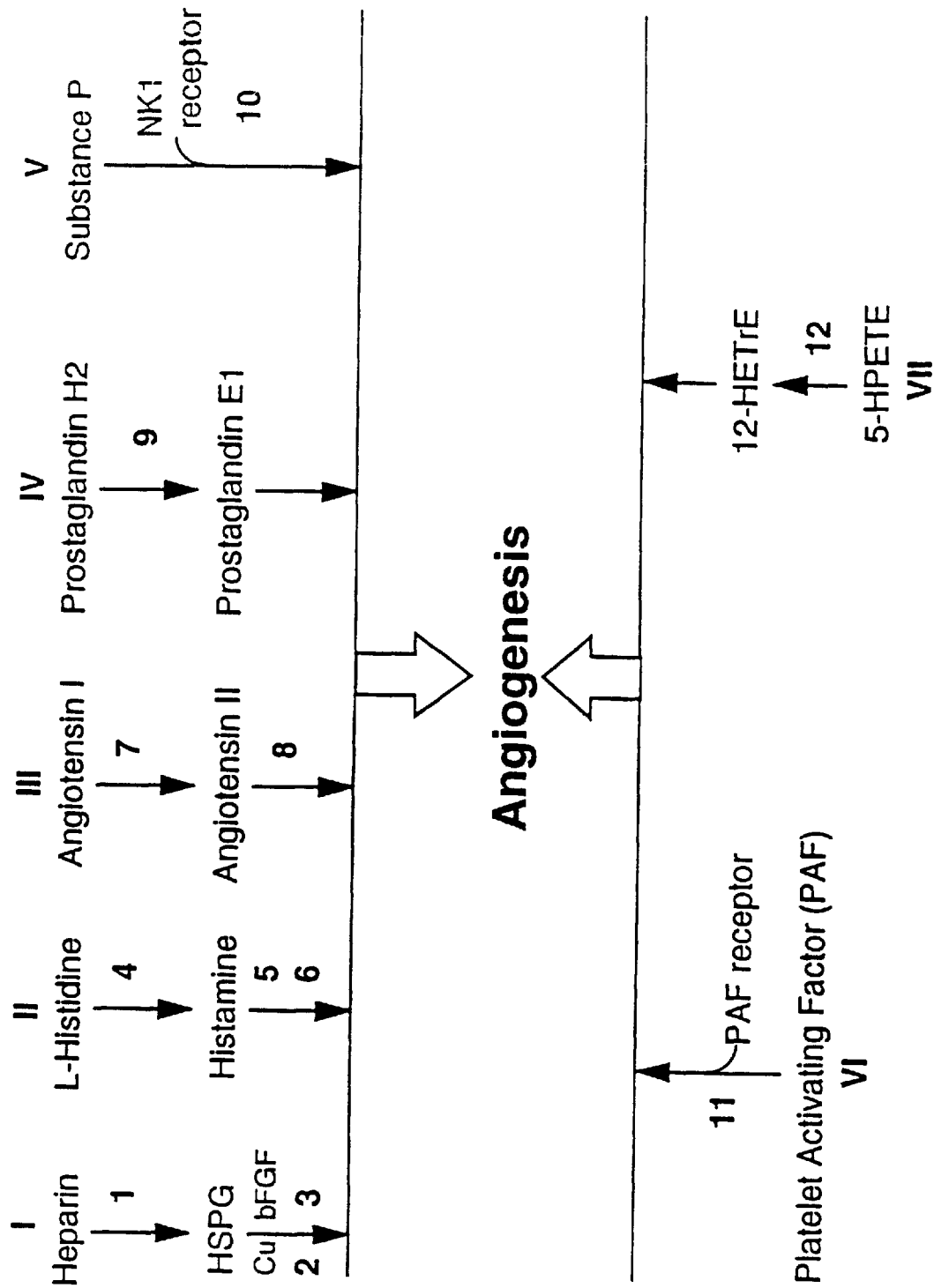

INHIBITION OF HAIR GROWTH

This is a continuation of application Ser. No. 08/396,446, filed Feb. 28, 1995, now abandoned.

BACKGROUND

The invention relates to a method of the inhibition of unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Angiogenesis, the development of new blood vessels, is the cumulative effect of many biochemical processes and occurs mainly during embryonic growth, wound healing, and the cyclical development of the uterine endometrium. Angiogenesis also plays a role in diabetic retinopathy, atherosclerosis, and tumor growth. Angiogenesis involves the degradation of both the parent vessel basement membrane and the interstitial matrix to provide a passage for the new vessel; migration of endothelial cells toward an angiogenic stimulus; formation of a lumen and the initiation of blood flow. These processes are under the control of growth factors, cytokines, peptides, immunomodulators, as well as other factors that may act as direct stimulants of angiogenesis or as indirect stimulants by attracting inflammatory factors.

There are at least seven major pathways thought to contribute to angiogenesis.

The first pathway involves heparin sulfate proteoglycans (HSPG). HSPG binds basic fibroblast growth factor (bFGF), and stimulates angiogenesis in the presence of copper ions. HSPG is formed from heparin by the enzyme sulfotransferase.

The second pathway involves histamine, which may stimulate angiogenesis after binding to specific histamine receptors. Histamine is formed from the amino acid histidine by the enzyme histidine decarboxylase (HDC). This synthetic reaction takes place in mast cells, and histamine is released from mast cells upon their degranulation.

The third pathway involves angiotensin II, which stimulates angiogenesis after binding to angiotensin II receptors. Angiotensin II is formed from angiotensin I by angiotensin converting enzyme (ACE).

The fourth pathway involves prostaglandin E1, which stimulates angiogenesis. Prostaglandin E1 synthesis is catalyzed by the enzyme prostaglandin synthase.

The fifth pathway involves Substance P, an endogenous molecule that functions as a neurotransmitter and in the regulation of inflammation. Substance P also possesses angiogenic properties by acting through the neurokinin 1 receptor (NK1).

The sixth pathway involves platelet activating factor (PAF), an endogenous protein that binds to a specific receptor and stimulates chemotaxis and leukocyte infiltration, which can lead to the stimulation of angiogenesis.

The seventh pathway involves the arachidonic acid metabolite 12(R)-HETrE, which is angiogenic through its effects on capillary permeability, neutrophil chemotaxis, vasodilation, and endothelial cell mitogenesis. The metabolite 12(R)-HETrE is formed from 5HETE by the enzyme cytochrome P450 reductase.

SUMMARY OF THE INVENTION

One aspect of the invention is the use of non-steroidal suppressors of angiogenesis to inhibit hair growth. It has now been found that unwanted mammalian (including human) hair growth—particularly androgen-stimulated hair growth—can be inhibited by applying to the skin a dermatologically acceptable composition including a non-steroidal suppressor of angiogenesis in an amount effective to reduce hair growth. The unwanted hair growth which is reduced may be normal hair growth, or hair growth that results from an abnormal or diseased condition.

Suppressors of angiogenesis include compounds that interfere with one or more of the seven major angiogenesis pathways described previously. There are at least 12 classes of compounds that have been found to interfere with one of these pathways, and thus can be used to inhibit hair growth. The 12 classes of compounds are set forth in the Figure.

Referring to the Figure, the first class of compounds inhibit the enzyme sulfotransferase. Examples include p-nitrocatechol and catechin. Inhibiting sulfotransferase interferes with the transformation of heparin to HSPG.

The second class of compounds are heparin binding antagonists, which inhibit the binding of HSPG to bFGF. Examples include pentosan polysulfate and quinacrine.

The third class of compounds are copper chelators, which also inhibit the binding of HSPG to bFGF. Examples include bathocuproine disulfonate and diethylenetriamine pentaacetic acid.

The fourth class of compounds inhibit the enzyme HDC. Examples include O-p-nitrohydroxylamine and α-fluoromethylhistidine. Inhibiting HDC interferes with the conversion of histidine to histamine.

The fifth class of compounds inhibit mast cell degranulation, and this interferes with the release of histamine from mast cells. Examples include mycophenolic acid, bromocryptine, and cromoglycate.

The sixth class of compounds are histamine receptor antagonists which interfere with the binding of histamine to specific histamine receptors. Examples include terfenadine, tripelennamine, chlorpheniramine, and cimetidine.

The seventh class of compounds inhibit ACE. Examples include enalapril and lisinopril. Inhibiting ACE interferes with the conversion of angiotensin I to angiotensin II.

The eighth class of compounds are angiotensin II receptor antagonists, which interfere with the binding of angiotensin II to specific angiotensin II receptors. Examples include 1,4-substituted indoles such as those described in Poss et al., Bioorganic & Medicinal Chemistry Letters, 4:145–150 (1994); dihydropyridine derivatives like nifedipine and others described in Webster et al., Bioorganic & Medicinal Chemistry Letters, 4:133–138 (1994); 2,4-dihydro-3H-1,2,4-triazol-3-ones (traizolinone) derivatives bearing a side chain at $N^4$ position as described by Chang et al. (Bioorganic & Medicinal Chemistry Letters, 4:115–120 (1994)); tetrahydroisoquinoline carboxylic acids; imidazopyridine derivatives like tetrahydroimidazopyridine carboxylic acid analogs; and Losartan.

The ninth class of compounds inhibit the enzyme prostaglandin synthetase. An example is piracetam. Inhibiting prostaglandin synthetase interferes with the formation of prostaglandin E1.

The tenth class of compounds are NK1 receptor antagonists, which interfere with the binding of Substance P to the NK1 receptor. Examples include (3aR,7aR)-7,7,-diphenyl-2-[1-imino-2-(2-methoxyphenyl)ethyl] perhydroisoindol-4-one and cis-2-(diphenylmethyl)-N-[(2-methoxy-phenyl)]-methyl]-1-azabicyclo[2,2,2]octan-3-amine.

The eleventh class of compounds are PAF receptor antagonists, which interfere with the binding of PAF to the PAF receptors. Examples include tioconazole and (3-[4-(2-chlorphenyl)-9-methyl-6H-thieno[2-f]-[1,2,4]triazolo-[4,3-a][1,4]-diazepin-2-yl-1-(4-morpholinyl)-1-propanone.

The twelfth class of compounds are inhibitors of the enzyme cytochrome P450 reductase. An example is clotrimazole. Inhibiting cytochrome P450 reductase interferes with the formation of 12(R)-HETrE from 5HETE.

Additional non-steroidal compounds that may inhibit angiogenesis—but which may not be members of one of the twelve classes of compounds described above—include phenyl-ethylene derivatives such as tamoxifen and nafoxidine; irsogladine; the synthetic laminin peptide, CDPGYIGSR-$NH_2$; radicicol; eponemycin; fumagillin (O-(chloroacetyl-carbamoyl)fumagillol) and synthetic analoges thereof; recombinant human platelet factor-4 and related peptides; protamine; sulfated chitin derivatives; diaminoanthraquinone derivatives; thrombospondin; quinoline-3-carboxamide (linomide); analogues of distamycin A; and aurintricarboxylic acid.

The above compounds are known and some are commercially available.

Another aspect of the invention features inhibiting mammalian hair growth by applying to the skin a dermatologically acceptable composition including an inhibitor of sulfotranferase.

Another aspect of the invention features inhibiting mammalian hair growth by applying to the skin a dermatologically acceptable composition including a heparin binding antagonist.

Another aspect of the invention features inhibiting mammalian hair growth by applying to the skin a dermatologically acceptable composition including a copper chelator.

Another aspect of the invention features inhibiting mammalian hair growth by applying to the skin a dermatologically acceptable composition including an inhibitor of HDC.

Another aspect of the invention features inhibiting mammalian hair growth by applying to the skin a dermatologically acceptable composition including an inhibitor of mast cell degranulation.

Another aspect of the invention features inhibiting mammalian hair growth by applying to the skin a dermatologically acceptable composition including a histamine receptor antagonist.

Another aspect of the invention features inhibiting mammalian hair growth by applying to the skin a dermatologically acceptable composition including an inhibitor of ACE.

Another aspect of the invention features inhibiting mammalian hair growth by applying to the skin a dermatologically acceptable composition including an angiotensin II receptor antagonist.

Another aspect of the invention features inhibiting mammalian hair growth by applying to the skin a dermatologically acceptable composition including an inhibitor of prostaglandin synthetase.

Another aspect of the invention features inhibiting mammalian hair growth by applying to the skin a dermatologically acceptable composition including an NKI receptor antagonist.

Another aspect of the invention features inhibiting mammalian hair growth by applying to the skin a dermatologically acceptable composition including a PAF receptor antagonist.

Another aspect of the invention features inhibiting mammalian hair growth by applying to the skin a dermatologically acceptable composition including an inhibitor of cytochrome P450 reductase.

Inhibitors of enzymes, and receptor antagonists, may be irreversible or reversible. Reversible inhibitors may be competitive or non-competitive.

"Non-steroidal", as used herein, means a compound that lacks the 17-carbon ring structure found typically in a steroid.

Other features and advantages of the invention will be apparent from the description of the embodiments thereof, and from the claim.

DRAWING

The FIGURE is a summary of twelve classes of compounds that interfere with angiogenesis.

EMBODIMENTS

The hair growth inhibiting compound is incorporated in a non-toxic dermatologically acceptable topical composition which preferably includes a vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the hair growth inhibiting compound in the composition may be varied over a wide range up to a saturated solution, preferably from 0.1% to 30% by weight or even more; the reduction of hair growth increases as the amount of compound applied increases per unit area of skin. The maximum amount effectively applied is limited only by the rate at which the hair growth inhibiting compound penetrates the skin. Generally, the effective amounts range from 100 to 3000 micrograms or more per square centimeter of skin.

The composition should be topically applied to a selected area of the body from which it is desired to inhibit hair growth. For example, the composition can be applied to the face, particularly to the beard area of the face, i.e., the cheek, neck, upper lip, and chin. The composition can also be applied to the legs, arms, torso or armpits. The composition is particularly suitable for inhibiting the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm in major diameter, which grow thick black and coarse hair similar to human beard hair. These organs produce hair in response to androgens in the hamster. To evaluate the effectiveness of a composition including a hair growth inhibiting compound, the flank organs of each of a group of hamsters are depilated by applying a thioglycolate based chemical depilatory (Surgex). To one organ of each animal 25 μl of vehicle alone once a day is applied, while to the other organ of each animal an equal amount of vehicle containing a hair growth inhibiting compound is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide an inhibition in hair growth of at least about 20%, more preferably at least about 40%, and most preferably at least about 60% when tested in the Golden Syrian hamster assay. A number of compositions were tested in the Golden Syrian hamster assay; the results are provided in the Table.

TABLE

| Compound | Dose | Vehicle* | pH | Hair Mass Treated(mg) | Control(mg) | % Inhibition |
|---|---|---|---|---|---|---|
| bathocuproine | 10% | A | 7.0 | 0.41 ± .06 | 2.23 ± .20 | 81 ± 3 |
| p-nitrocatechol sulfate | 10% | A | 9.0 | 0.58 ± .08 | 2.39 ± .21 | 74 ± 5 |
| aurintricarboxylic acid | 10% | A | 4.0 | 0.92 ± .08 | 2.70 ± .29 | 66 ± 2 |
| mycophenolic acid | 10% | D | 4.0 | 0.60 ± .13 | 1.85 ± .19 | 65 ± 8 |
| nafoxidine | 10% | A | 5.0 | 0.76 ± .19 | 1.70 ± .14 | 59 ± 8 |
| tamoxifen | 10% | A | 4.5 | 0.72 ± .17 | 1.65 ± .24 | 56 ± 12 |
| catechin | 10% | A | 4.5 | 0.56 ± .12 | 1.31 ± .12 | 56 ± 8 |
| quinacrine | 10% | A | 6.0 | 1.27 ± .23 | 2.50 ± .40 | 50 ± 8 |
| O-p-nitrohydroxylamine | 10% | A | 4.0 | 0.94 ± .17 | 1.82 ± .21 | 50 ± 5 |
| diethylenetriamine pentaacetic acid | 7.5% | B | 4.0 | 1.31 ± .22 | 2.44 ± .28 | 49 ± 8 |
| cimetidine | 10% | A | 8.0 | 0.95 ± .14 | 1.85 ± .23 | 46 ± 7 |
| lisinopril | 7.5% | A | 5.0 | 0.79 ± .14 | 1.50 ± .23 | 44 ± 10 |
| piracetam | 10% | A | 6.0 | 0.89 ± .18 | 1.44 ± .22 | 38 ± 10 |
| enalapril | 10% | C | 5.0 | 1.25 ± .16 | 2.06 ± .11 | 38 ± 9 |
| pentosan polysulfate | 10% | A | 6.5 | 1.07 ± .16 | 1.57 ± .12 | 33 ± 7 |
| terfenadine | 5% | B | 8.0 | 1.50 ± .26 | 2.18 ± .26 | 32 ± 8 |
| tripelennamine | 10% | A | 6.5 | 1.20 ± .23 | 1.80 ± .23 | 30 ± 9 |
| chlorfeniramine | 10% | A | 6.0 | 0.92 ± .16 | 1.40 ± .21 | 29 ± 12 |
| tranexamic acid | 10% | A | 5.5 | 1.47 ± .13 | 2.01 ± .15 | 21 ± 12 |

*vehicle A = 68% $H_2O$; 16% ethanol; 5% propylene glycol; 4% benzyl alcohol; 2% propylene carbonate
B = 80% $H_2O$; 10% dipropylene glycol; 10% ethanol
C = 80% ethanol; 17.5% $H_2O$; 2% propylene glycol dipelargonate; 0.5% propylene glycol
D = 70% ethanol; 30% dimethylsulfoxamine It will be appreciated by those skilled in the art that the invention can be performed within a wide range of equivalent parameters of composition and conditions without departing from the spirit or scope of the invention or of any embodiment thereof.

We claim:

1. A method of reducing human androgen-stimulated hair growth which comprises
   selecting an area of skin on a human from which reduced androgen-stimulated hair growth is desired; and
   applying to said area of skin a dermatologically acceptable composition comprising a non-steroidal suppressor of angiogenesis in an amount effective to reduce androgen-stimulated hair growth.

2. The method of claim 1, wherein said suppressor is a compound that interferes with the action of heparin sulfate proteoglycans.

3. The method of claim 2, wherein said compound is an inhibitor of sulfotransferase.

4. The method of claim 2, wherein said compound is a heparin binding antagonist.

5. The method of claim 2, wherein said compound is a copper chelator.

6. The method of claim 1, wherein said suppressor is a compound that interferes with the action of histamine.

7. The method of claim 6, wherein said compound is an inhibitor of histidine decarboxylase.

8. The method of claim 1, wherein said suppressor is a compound that is an inhibitor of mast cell degranulation.

9. The method of claim 6, wherein said compound is a histamine receptor antagonist.

10. The method of claim 1, wherein said suppressor is a compound that interferes with the action of angiotensin II.

11. The method of claim 10, wherein said compound is an inhibitor of angiotensin converting enzyme.

12. The method of claim 10, wherein said compound is an angiotensin II receptor antagonist.

13. The method of claim 1, wherein said suppressor is a compound that interferes with the action of prostaglandin E1.

14. The method of claim 1, wherein said suppressor is a compound that is an inhibitor of prostaglandin synthetase.

15. The method of claim 1 wherein said suppressor interferes with the action of Substance P.

16. The method of claim 15, wherein said compound is an NK1 receptor antagonist.

17. The method of claim 1, wherein said suppressor interferes with the action of platelet activating factor.

18. The method of claim 17, wherein said compound is a platelet activating factor receptor antagonist.

19. The method of claim 1, wherein said suppressor interferes with the action of 12-HETrE.

20. The method of claim 19, wherein said compound is an inhibitor of cytochrome P450 reductase.

21. The method of claim 1, wherein said composition further comprises vehicle.

22. The method of claim 1, wherein the concentration of said suppressor in said composition is between 1% and 30% by weight.

23. The method of claim 1, wherein the composition provides a reduction in hair growth of at least 20% when tested in the Golden Syrian hamster assay.

24. The method of claim 1, wherein the composition provides a reduction in hair growth of at least 50% when tested in the Golden Syrian hamster assay.

25. The method of claim 1, wherein the composition provides a reduction in hair growth of at least 70% when tested in the Golden Syrian hamster assay.

26. The method of claim 1, wherein the suppressor is applied to the skin in an amount of from 100 to 3000 micrograms of said inhibitor per square centimeter of skin.

27. The method of claim 1, wherein said area of skin is on the face of the human.

28. The method of claim 27, wherein said human is a woman suffering from hirsutism.

29. A method of reducing mammalian hair growth which comprises
   selecting an area of skin from which reduced hair growth is desired; and
   applying topically to said area of skin a dermatologically acceptable composition comprising an inhibitor of sulfotransferase in an amount effective to reduce hair growth.

30. The method of claim 29, wherein said inhibitor is p-nitrocatechol.

31. The method of claim 29, wherein said inhibitor is catechin.

32. A method of reducing mammalian hair growth which comprises
   selecting an area of skin from which reduced hair growth is desired; and
   applying topically to said area of skin a dermatologically acceptable composition comprising a heparin binding antagonist in an amount effective to reduce hair growth.

33. The method of claim 32, wherein said antagonist is pentosan polysulfate.

34. The method of claim 32, wherein said antagonist is quinacrine.

35. A method of reducing mammalian hair growth which comprises
   selecting an area of skin from which reduced hair growth is desired; and
   applying topically to said area of skin a dermatologically acceptable composition comprising a copper chelator in an amount effective to reduce hair growth.

36. The method of claim 35, wherein said copper chelator is bathocuproine disulfonate.

37. The method of claim 35, wherein said copper chelator is diethylenetriamine pentaacetic acid.

38. A method of reducing mammalian hair growth which comprises
   selecting an area of skin from which reduced hair growth is desired; and
   applying to said area of skin a dermatologically acceptable composition comprising an inhibitor of histidine decarboxylase in an amount effective to reduce hair growth.

39. The method of claim 38, wherein said inhibitor is O-p-nitrohydroxylamine.

40. The method of claim 38, wherein said inhibitor is α-fluoromethylhistidine.

41. A method of reducing human androgen-stimulated hair growth which comprises
   selecting an area of skin on a human from which reduced androgen-stimulated hair growth is desired; and
   applying to said area of skin a dermatologically acceptable composition comprising an inhibitor of mast cell degranulation in an amount effective to reduce androgen-stimulated hair growth.

42. The method of claim 41, wherein said inhibitor is mycophenolic acid.

43. The method of claim 41, wherein said inhibitor is bromocryptine.

44. The method of claim 41, wherein said inhibitor is cromoglycate.

45. A method of reducing mammalian hair growth which comprises
   selecting an area of skin from which reduced hair growth is desired; and
   applying topically to said area of skin a dermatologically acceptable composition comprising a histamine receptor antagonist in an amount effective to reduce hair growth.

46. The method of claim 45, wherein said antagonist is terfenadine.

47. The method of claim 45, wherein said antagonist is tripelennamine.

48. The method of claim 45, wherein said antagonist is chlorpheniramine.

49. The method of claim 45, wherein said antagonist is cimetidine.

50. A method of reducing mammalian hair growth which comprises
   selecting an area of skin from which reduced hair growth is desired; and
   applying topically to said area of skin a dermatologically acceptable composition comprising an inhibitor of angiotensin converting enzyme in an amount effective to reduce hair growth.

51. The method of claim 50, wherein said inhibitor is enalapril.

52. The method of claim 50, wherein said inhibitor is lisinopril.

53. A method of reducing mammalian hair growth which comprises
   selecting an area of skin from which reduced hair growth is desired; and applying topically to said area of skin a dermatologically acceptable composition comprising an angiotensin II receptor antagonist in an amount effective to reduce hair growth.

54. The method of claim 53, wherein said antagonist is a 1,4-substituted indole.

55. The method of claim 53, wherein said antagonist is a dihydropyridine derivative.

56. The method of claim 55, wherein said antagonist is nifedipine.

57. The method of claim 53, wherein said antagonist is a triazolinone derivative.

58. The method of claim 57, wherein said triazolinane derivative has a side chain at the $N^4$ position.

59. The method of claim 53, wherein said antagonist is a tetrahydroisoquinoline carboxylic acid.

60. The method of claim 53, wherein said antagonist is an imidazopyridine derivative.

61. The method of claim 60, wherein said imidazopyridine derivative is a tetrahydroimidazopyridine carboxylic acid analog.

62. The method of claim 53, wherein said antagonist is Losantan.

63. A method of reducing mammalian hair growth which comprises selecting an area of skin from which reduced hair growth is desired; and applying topically to said area of skin a dermatologically acceptable composition comprising an inhibitor of prostaglandin synthetase in an amount effective to reduce hair growth.

64. The method of claim 63, wherein said inhibitor is piracetam.

65. A method of reducing mammalian hair growth which comprises selecting an area of skin from which reduced hair growth is desired; and applying topically to said area of skin a dermatologically acceptable composition comprising an $NK^1$ receptor antagonist in an amount effective to reducing hair growth.

66. The method of claim 65, wherein said antagonist is (3aR,7aR)-7,7,-diphenyl-2-[1-imino-2-(2-methoxyphenyl) ethyl]perhydroisoindol-4-one.

67. The method of claim 65, wherein said antagonist is cis-2-(diphenylmethyl)-N-[(2-methoxy-phenyl)]-methyl]-1-azabicyclo[2,2,2]octan-3-amine.

68. A method of reducing mammalian hair growth which comprises selecting an area of skin from which reduced hair growth is desired; and applying topically to said area of skin a dermatologically acceptable composition comprising a platelet activating factor receptor antagonist in an amount effective to reduce hair growth.

69. The method of claim 68, wherein said antagonist is tioconazole.

70. The method of claim 68, wherein said antagonist is (3-[4-(2-chlorphenyl)-9-methyl-6H-thieno[2-f]-[1,2,4] triazolo-[4,3-a][1,4]-diazepin-2-yl-1-(4-morpholinyl)-1-propanone.

71. A method of reducing mammalian hair growth which comprises selecting an area of skin from which reduced hair growth is desired; and applying topically to said area of skin a dermatologically acceptable composition comprising an inhibitor of cytochrome P450 reductase in an amount effective to reduce hair growth.

72. The method of claim 71, wherein said inhibitor is clotrimazole.

73. The method of claim 1 or 41, wherein said area of skin comprises the beard area.

74. A method of reducing mammalian hair growth which comprises selecting an area of skin from which reduced hair growth is desired; and applying topically to said area of skin a dermatologically acceptable composition comprising, in an amount effective to reduce hair growth, a compound selected from the group consisting of tamoxifen; nafoxidine; irsogladine; the synthetic laminin peptide, CDPGYIGSR-$NH_2$; radicicol; eponemycin; fumagillin (O-(chloroacetyl-carbamoyl)fumagillol) and synthetic analogues thereof; recombinant human platelet factor-4 and related peptides; protamine; sulfated chitin derivatives; diaminoanthraquinone derivatives; thrombospondin; quinoline-3-carboxamide (linomide); analogues of diatamycin A; and aurintricarboxylic acid.

75. The method of claim 74, wherein said compound is tamoxifen.

76. The method of claim 74, wherein said compound is nafoxidine.

77. The method of claim 74, wherein said compound is CDPGYIGSR-$NH_2$.

78. The method of claim 74, wherein said compound is radicicol.

79. The method of claim 74, wherein said compound is eponemycin.

80. The method of claim 74, wherein said compound is fumagillin.

81. The method of claim 74, wherein said compound is recombinant human platelet factor-4.

82. The method of claim 74, wherein said compound is protamine.

83. The method of claim 74, wherein said compound is thrombospondin.

84. The method of claim 74, wherein said compound is quinoline-3-carboxamide.

85. The method of claim 74, wherein said compound is aurintricarboxylic acid.

86. The method of claim 29, 32, 35, 38, 45, 50, 53, 63, 65, 68, 71, or 74, wherein said area of skin is on a human.

87. The method of claim 1, 29, 32, 35, 38, 41, 45, 50, 53, 63, 65, 68, 71, or 74, wherein said area of skin is on the face or body of a human.

88. The method of claim 1, 29, 32, 35, 38, 41, 45, 50, 53, 63, 65, 68, 71, or 74, wherein said area of skin is on a human and said hair growth comprises androgen-stimulated hair growth.

* * * * *

(12) EX PARTE REEXAMINATION CERTIFICATE (7071st)
United States Patent
Ahluwalia et al.

(10) Number: US 6,093,748 C1
(45) Certificate Issued: Sep. 22, 2009

(54) INHIBITION OF HAIR GROWTH

(76) Inventors: Gurpreet S. Ahluwalia, 8632 Stable View Ct., Gaithersburg, MD (US) 20879; Peter Styczynski, 3709 Roop Rd., New Windsor, MD (US) 21776; Douglas Shander, 16112 Howard Landing Dr., Gaithersburg, MD (US) 20878

Reexamination Request:
No. 90/010,178, May 23, 2008

Reexamination Certificate for:
Patent No.: 6,093,748
Issued: Jul. 25, 2000
Appl. No.: 08/963,227
Filed: Nov. 3, 1997

Related U.S. Application Data

(63) Continuation of application No. 08/396,446, filed on Feb. 28, 1995, now abandoned.

(51) Int. Cl.
| | |
|---|---|
| A61K 8/30 | (2006.01) |
| A61K 8/73 | (2006.01) |
| A61K 8/72 | (2006.01) |
| A61K 8/66 | (2006.01) |
| A61Q 7/02 | (2006.01) |

(52) U.S. Cl. .................. 514/183; 424/74; 514/844; 514/874; 514/2; 514/220; 514/250
(58) Field of Classification Search .................. None
See application file for complete search history.

(56) References Cited

U.S. PATENT DOCUMENTS

| 4,720,489 A | 1/1988 | Shander ................. 514/171 |
| 5,178,883 A | 1/1993 | Knighton ................ 424/532 |
| 5,411,991 A | 5/1995 | Shander et al. ........... 514/665 |

FOREIGN PATENT DOCUMENTS

| WO | WO 90/12577 | 11/1990 |
| WO | WO 91/19731 | 12/1991 |

OTHER PUBLICATIONS

Cohen et al. Current Eye Research 1994, 13:139–144.*
Laniado–Schwartzman et al. J. Biol. Chem. 1994, 269:24321–24327.*
Ziche et al. JNCI 1982, 69:475–480.*
Folkman et al. J. Biol. Chem. 1992, 267:10931–10934.*
Fan et al. Br. J. Pharmacol. 1993, 110:43–49.*
White et al. Principles of Biochemistry. Sixth Edition. McGraw Hill Book Company. 1978. pp. 637–638, 720, 1150.*
Gagliardi et al., 1992, *Cancer Research* 52:5073–5075, "Inhibition of Angiogenesis by Suramin".
Ingber et al., 1990, *Nature* 348:555–557, "Synthetic analogues of fumagillin that inhibit angiogenesis and suppress tumour growth".
Jasnis et al., 1994, *Cancer Letters* 79:39–43, "Polyamines prevent DFMO–mediated inhibition of angiogenesis".
LaRochelle et al., 1993, *Cell Growth & Differentiation* 4:547–553, "Inhibition of Platelet–derived Growth Factor Autocrine Growth Stimulation by a Monoclonal Antibody to the Human α Platelet–derived Growth Factor Receptor".
Matsubara et al., 1989, *Journal of Clinical Investigation* 83:158–167, "Inhibition of Human Endothelial Cell Proliferation In Vitro and Neovascularization In Vivo by α–Penicillamine".
Takigawa et al., 1990, *Cancer Research* 50:4131–4138, "Tumor Angiogenesis and Plyamines; α–Difluoromethylomithine, an Irreversible Inhibitor of Ornithine Decarboxylase, Inhibits B16 Melanoma–induced Angiogenesis in Ovo and the Proliferation of Vascular Endothelial Cells in Vitro".
Vaisman et al., 1990, *The Journal of Cell Biology* 265(2):19461–19466 "Characterization of the Receptors for Vascular Endothelial Growth Factor".
Vapaatalo et al., 1979, *Agents and Actions: Supplements* AAS5:85–98, "Connective Tissue Changes in Rheumatoid Arthritis and the Use of Penicillamine".
Volpert et al., 1996, *Journal of Clinical Investigation* 98(3):671–679, "Captapril Inhibits Angiogenesis and Slows the Growth of Experimental Tumors in Rats".
Wang and Prewitt, 1990, *Hypertension* 15(1):68–77, "Captopril Reduces Aortic and Microvascular Growth in Hypertensive and Normotensive Rats".
Zugmaier 1992 J. National Cancer Institute 84:1716–1724.

* cited by examiner

*Primary Examiner*—Evelyn Huang

(57) ABSTRACT

A method of inhibiting hair growth in a mammal includes applying, to an area of skin from which reduced hair growth is desired, a dermatologically acceptable composition containing a non-steroidal suppressor of angiogenesis.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–88 are cancelled.

* * * * *